United States Patent
Schwarz

(10) Patent No.: US 7,430,042 B2
(45) Date of Patent: Sep. 30, 2008

(54) DEVICE AND METHOD FOR DETERMINING THE PROPERTIES OF SURFACES

(75) Inventor: Peter Schwarz, Königsdorf (DE)

(73) Assignee: BYK Gardner GmbH, Geretsried (DE)

( * ) Notice: Subject to any disclaimer, the term of this patent is extended or adjusted under 35 U.S.C. 154(b) by 338 days.

(21) Appl. No.: 10/912,831

(22) Filed: Aug. 6, 2004

(65) Prior Publication Data

US 2005/0030542 A1 Feb. 10, 2005

(30) Foreign Application Priority Data

Aug. 8, 2003 (DE) ................. 103 36 493

(51) Int. Cl.
*G01N 21/00* (2006.01)

(52) U.S. Cl. .................... 356/237.2

(58) Field of Classification Search ........... None
See application file for complete search history.

(56) References Cited

U.S. PATENT DOCUMENTS

| | | | | |
|---|---|---|---|---|
| 4,501,961 A | * | 2/1985 | Stauffer | ............... 356/4.03 |
| 4,750,140 A | * | 6/1988 | Asano et al. | ............... 356/445 |
| 4,980,626 A | * | 12/1990 | Hess et al. | ............... 250/559.33 |
| 5,448,078 A | * | 9/1995 | Nakazawa | ............... 250/559.24 |
| 5,712,489 A | * | 1/1998 | Elvidge et al. | ............... 356/429 |
| 5,760,893 A | * | 6/1998 | Raymond | ............... 356/237.1 |
| 5,963,328 A | | 10/1999 | Yoshida et al. | |
| 6,094,270 A | * | 7/2000 | Uomori et al. | ............... 356/623 |
| 6,276,586 B1 | * | 8/2001 | Yeo et al. | ............... 226/17 |
| 6,327,520 B1 | * | 12/2001 | Hooker et al. | ............... 356/614 |
| 6,847,859 B2 | * | 1/2005 | Nuebling et al. | ............... 356/602 |

FOREIGN PATENT DOCUMENTS

WO WO 02/093109 A1 11/2002

* cited by examiner

*Primary Examiner*—Gregory J. Toatley, Jr.
*Assistant Examiner*—Juan D Valentin
(74) *Attorney, Agent, or Firm*—Greer, Burns & Crain, Ltd.

(57) ABSTRACT

Device for determining the properties of surfaces having at least one first radiation means having at least one first radiation source which directs a predetermined radiation towards a measurement surface; at least one first radiation detector means which captures at least a portion of the radiation reflected and/or diffused off the measurement surface and emits at least one measurement signal which is characteristic of the reflected and/or diffused radiation, wherein at least one second radiation means is provided which directs at least partially directional radiation at a predetermined angle towards the measurement surface, and at least one second radiation detector means having a predetermined radiation detector surface, which at least partially captures the radiation emitting from the second radiation means and reflected off the measurement surface, and determines its position on the detector surface.

32 Claims, 3 Drawing Sheets

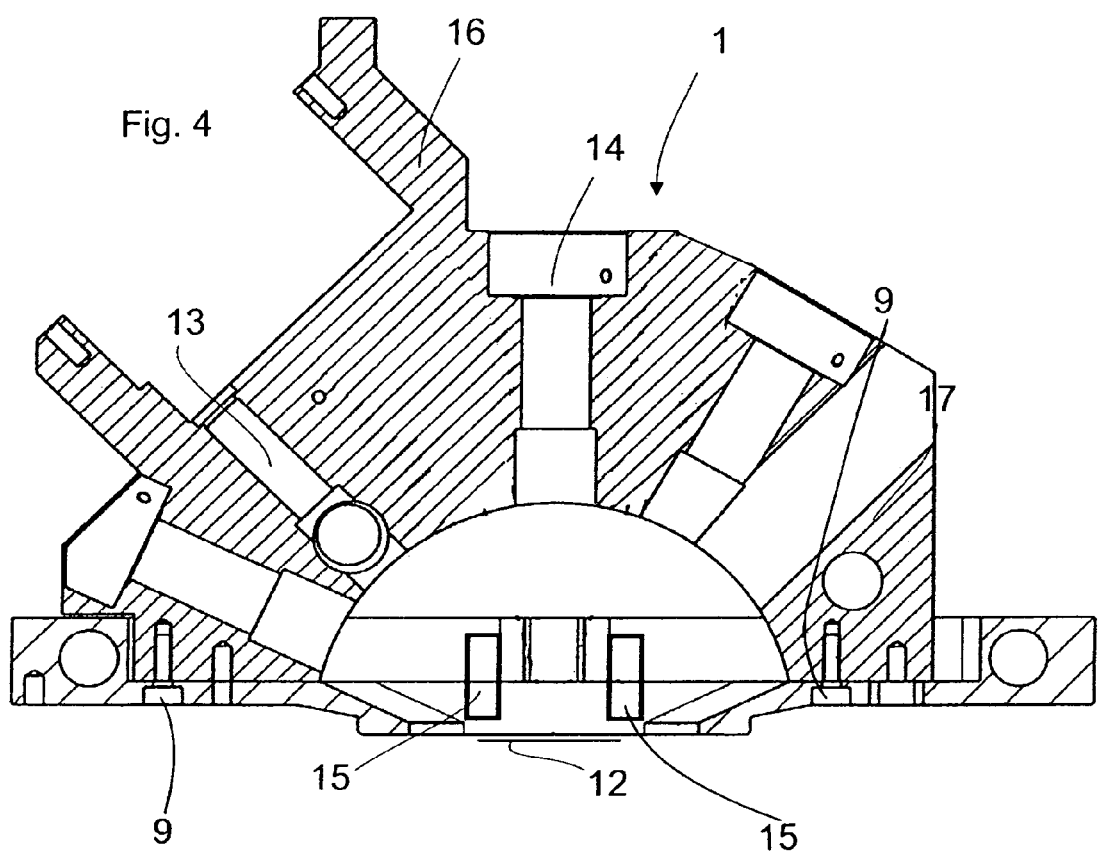

DEVICE AND METHOD FOR DETERMINING THE PROPERTIES OF SURFACES

FIELD OF THE INVENTION

The present invention relates to a device and a method for determining the properties of surfaces.

BACKGROUND OF THE INVENTION

The quality of surfaces is a significant property of objects used in everyday life such as furnishings and consumer items such as cars and the like, thus decisively determining the overall impression on a human observer. An example therefor are high-gloss or metallic finishes of car bodies or marbled effects of industrially manufactured objects or their surfaces.

The reproducible evaluation of the quality of surfaces in particular of said high-gloss finishes requires measuring instruments which capture precisely those physical quantities which decisively determine the overall impression on a human observer. Various methods and devices are known in the prior art for determining the visual properties and specifically the reflection and diffusion characteristics of surfaces.

With these devices and also the corresponding measuring methods, attention must be paid to that the device be arranged in a predetermined or defined angular position relative the finish, for example it is manually guided parallel to it. This is of decisive significance because the reflection and diffusion characteristics vary dramatically even with small angle variations dependent on said angular position.

SUMMARY OF THE INVENTION

Thus it is the object of the present invention to provide a device that determines the angular position of the device relative the surface to be measured and allows the operator to set a specified angular position.

This object is solved by the device of claim 1 and the method of claim 27. Preferred embodiments are the subject of the subclaims.

The device of the present invention for determining the properties of surfaces comprises at least one first radiation means having at least one first radiation source which directs a predetermined radiation towards a measurement surface. In addition, at least one first radiation detector means is provided which captures at least a portion of the radiation reflected and/or diffused off the measurement surface and emits at least one measurement signal which is characteristic of the reflected and/or diffused radiation.

Preferably said device comprises at least one adjustment means by means of which the angular position of the device relative the measurement surface can be varied.

Preferably at least one radiation means is provided which directs at least partially directional radiation at a predetermined angle towards the measurement surface, and at least one second radiation detector means having a predetermined radiation detector surface which at least partially captures the radiation emitting from said second radiation means and reflected off the measurement surface when the device is positioned at a predetermined angular position relative the measurement surface.

The device therefore comprises at least one measurement means which determines the position of the device relative the measurement surface. Position is understood to mean the distance and the angular position between the device and the measurement surface.

Within the scope of the present invention, measurement surface is understood to mean in particular a predetermined segment of a car body or the finish of a car body in particular of motor vehicles. In addition the device could also be used for measuring the marbled effect or color patterns of plastic surfaces.

At least partially directional radiation is understood to mean that the light is not diffused. For example laser light or light concentrated by lenses is understood to mean at least partially directional radiation in the sense of the invention. Radiation detector surface is understood to mean the surface onto which the radiation to be measured impinges, for example a photodiode array.

A predetermined angular position of the device relative the measurement surface is understood to mean that the position of the device relative the surface is spatially defined, for example tangential relative the measurement surface. The angular position may relate to one plane only but the angular position is preferably to be understood spatially, i.e. that in every preferred direction the device has a predetermined angular position relative the measurement surface.

As will be explained in more detail below, the device is preferably displaced relative the measurement surface such that the distance between the device and the measurement surface remains substantially constant. The device may be displaced on a predetermined plane at least in segments.

A tangential angular position of the device relative the measurement surface according to the present invention is to be understood such that the plane on which the device is displaced at least in segments, is substantially tangential relative the measurement surface or relative a predetermined point of the measurement surface or substantially parallel to such a tangential plane.

The tangential plane contacts the measurement surface at a predetermined point and is perpendicular to a geometrical connecting line from the point of contact to a specified central point of the surface segment. In the case of a sphere this is the connecting line from the point of contact to the center of the sphere.

Within the scope of the invention, properties of a surface or properties of a textured surface are in particular understood to mean such physical properties of a surface which specify or characterize the appearance of a surface to a human observer. These include above all properties such as macro- und micro-texture, topography, color, color location, color transition, contrast, streaks, color brightness, gloss, distinctness of image (DOI), haze, surface textures and orange peel etc.

In another embodiment the device comprises at least one first radiation means having at least one first radiation source and directing a predetermined radiation at a measurement surface. In addition, at least one first radiation detector means is provided which captures at least a portion of the radiation reflected and/or diffused off the measurement surface and emits at least one measurement signal which is characteristic of the reflected and/or diffused radiation.

The device comprises at least one distance measurement means for determining the distance from a predetermined geometrical location of the device to the measurement surface.

In addition, preferably at least one adjustment means is provided by means of which the angular position of the device relative the measurement surface can be varied.

The distance of a predetermined location of the device is understood such that not the distance of the entire device is measured but that of a specifically selected point, for example the location of the distance measurement means. Likewise it is not the distance to the measurement surface that is determined but again the distance to a specific geometrical point of the measurement surface. Distance may also be understood to mean the smallest geometrical distance between the measurement surface and the device.

In another preferred embodiment the predetermined radiation detector surface is irradiated non-uniformly by radiation emitting from the second radiation means. This is to be understood such that some surface segments of the radiation detector surface are irradiated more or less intensively compared to other surface segments.

Conversely, uniform irradiation is to be understood such that substantially the entire radiation detector surface is irradiated at substantially the same intensity such as occurs for example with diffused light. In a preferred embodiment, a light beam having an increased intensity in a preferred area, for example in its center, and in the edge areas a lower intensity, impinges on the radiation detector surface or a predetermined surface segment of the radiation detector surface.

In another preferred embodiment, only selected areas of the radiation detector surface are irradiated with radiation emitting from the second radiation means, wherein the location of said areas substantially depends on the angular position of the device relative the measuring surface. If the device is oriented precisely tangential relative the measurement surface then for example the radiation or the geometrical center having the highest radiation intensity can substantially hit the geometrical center of the radiation detector surface.

In another preferred embodiment, the device comprises a plurality of adjustment means by means of which the device can be positioned in a preferred angular direction relative the measurement surface. In this case for example two adjustment means may be provided which allow varying the angular position in two directions perpendicular to each other.

In a preferred embodiment the adjustment means may comprise screws, in particular but not exclusively micrometer screws.

In another preferred embodiment the second radiation detector means comprises a plurality of capturing components. The capturing components may be in particular but are not exclusively photodiodes or photocells.

In another preferred embodiment said second radiation detector means is connected with at least one indicator means which outputs measures for the location on the second radiation detector means on which a predetermined portion of the radiation emitting from said second radiation detector means impinges. Thus it is conceivable for example to image the radiation detector surface onto a monitor or the like and/or indicate at what intensity the radiation impinges on which areas of the radiation detector surface. In this way the operator can set the individual adjusting means and thus adjust the device relative the measurement surface such that it is tangential towards it which becomes apparent in a preferred embodiment by the radiation impinging substantially on the center of the radiation detector surface and thus the indicator means displays the radiation impinging on the center of the detector surface.

Additionally the indicator means may be designed such that the operator is shown for example by symbols the angular position of the device relative the measurement surface, or that the operator is instructed in particular but not exclusively as to necessary changes to the individual indicator means.

In addition to or instead of an indicator means, automatic means are conceivable to automatically adjust the angular position. In this case, individual adjusting means may be provided in particular but not exclusively having servo motors which, in reaction to the radiation impinging on the second radiation detector surface or the irradiated segments, unassistedly set the angular position so as to achieve for example a tangential angular position. A combination of manual and automatic adjustment is also conceivable.

In another preferred embodiment the measured angular position is taken into account for evaluating and/or computing the measurement result. In this case it is preferred that the device is not adjusted tangentially or in a predetermined position but a determined deviation from the predetermined position is taken into account for evaluating the measurement results.

In another preferred embodiment a plurality of capturing components of the second radiation detector means is distributed substantially concentrically around a predetermined geometrical center. It is for example possible to distribute four or more capturing components such as photodiodes or photocells around a geometrical center.

Such a device may also serve to adjust the angular position of the device relative the measurement surface by adjusting the radiation beam emitting from the second radiation means such that substantially all of the capturing components are irradiated at substantially the same intensity. It is assumed that the radiation has a substantially circular profile.

This will also allow, in cases of different profiles such as in particular but not exclusively substantially elliptic profiles, to achieve such adjustment by positioning the device such that radiation onto photocells opposed to each other will exhibit substantially the same intensity.

This method serves to achieve that the maximum intensity of the radiation preferably found substantially in the geometrical center of a beam will not hit a photocell, thus preventing destruction.

In another preferred embodiment the second radiation detector means emits a signal which serves to adjust the angular position of the device relative the measurement surface. In this instance for example averaging can be carried out via the capturing components which are substantially in the geometrical center region of the radiation detector surface. Adjustment can be carried out such that the displayed intensity values become the maximum. An automatic adjustment as described above in particular but not exclusively by means of servo motors is also within the scope of the invention.

In another preferred embodiment the device comprises a measuring aperture through which the radiation impinges on the measurement surface.

In another preferred embodiment a plurality of distance measurement means is provided which are arranged at predetermined positions relative the measuring aperture. Here it is for example possible to arrange the individual distance means concentrically around the aperture so as to achieve a substantially tangential adjustment of the device relative the measurement surface by means of the measured distances on the measurement surface.

Preferably at least one distance measurement means comprises at least one component from a group of components including radiation sources, magnetic components, in particular but not exclusively magnet coils, capacitive components, components utilizing the Hall effect or the like.

In a preferred embodiment at least one, preferably each, distance measurement means emits a signal which is characteristic of the distance from the specified geometrical location of the device to the measurement surface. As mentioned above, adjustment of the individual signals may serve to bring the device into a predetermined angular position relative the measurement surface, for example in a tangential position relative the measurement surface.

A tangential angular position of the device relative the measurement surface is understood to mean, in addition to the above definition, that a perpendicular dropped onto the geometrical center of the aperture is perpendicular to the area of the measurement surface directly beneath the aperture. This means that the cross-sectional area of the aperture and the cross-sectional area of the measurement surface are at least partially parallel to one another. This means that the plane on which the aperture cross-section lies and the plane on which the device is displaced relative the measurement surface are substantially parallel.

In another preferred embodiment the radiation means comprises at least one radiation source selected from a group of radiation sources comprising lasers, coherent and non-coherent semiconductor radiation sources, thermal radiation sources, in particular but not exclusively light bulbs, halogen light bulbs and the like. In another preferred embodiment the second radiation means comprises radiation directing means, in particular but not exclusively lenses and the like.

In another preferred embodiment the radiation emitting from the first radiation means is at least partially collimated by at least one radiation directing means.

In another preferred embodiment at least one radiation directing means comprises at least one radiation directing component selected from a group of radiation directing components comprising lens elements, micro lens elements, micro lens arrays, diffracting components, reflector components, in particular but not exclusively parabolic reflectors, grating components, volume grating components, holographic components and the like.

In another preferred embodiment at least one radiation means comprises a diaphragm means such as in particular but not exclusively an apertured diaphragm positioned in the path of radiation between the radiation means and the measurement surface.

In another preferred embodiment the radiation emitting from the second radiation means is repeatedly reflected in its optical path to the second radiation detector means. In this way it can be achieved that deviations caused by an angular position departing from a tangent will also be amplified.

In another preferred embodiment the predetermined angle at which the radiation emitting from the second radiation means impinges on the measurement surface is between 0 and 90°, preferred between 0 and 60°, particularly preferred between 0 and 45° and in particular between 0 and 30°.

In another preferred embodiment at least the first radiation means comprises a radiation diffusor means selected from a group of radiation diffusor means comprising radiation diffusor disks, frosted glass disks, diffusor films and the like.

In another preferred embodiment at least the first and/or the second radiation means are mounted in a housing above the measurement surface. Preferably the second radiation means comprises a radiation source such as in particular but not exclusively a laser source. Said laser source is selected from a group of laser sources comprising gas lasers such as in particular but not exclusively helium-neon lasers, semiconductor lasers, polymer lasers and the like.

Preferably at least the first and/or the second radiation means is variable relative one radiation parameter which is selected from a group of parameters comprising radiation intensity, radiation wavelength, direction of radiation polarization, temporal radiation intensity modulation and the like.

In another preferred embodiment the device is preferably movable relative the measurement surface such that the distance between the radiation means and the measurement surface remains substantially constant. This means that the device can be displaced substantially in a tangential direction relative the measurement surface.

In a further preferred embodiment at least one distance measurement means is provided which emits at least one measurement signal which is characteristic of the distance of the relative movement from the device to the measurement surface. Such measurement means may in particular but not exclusively be provided in at least one of the wheels mounted at the device.

In another preferred embodiment the device comprises at least one coating-thickness measurement means for determining the coating thickness of the surface to be examined wherein said coating-thickness measurement means comprises at least one coating thickness sensor which emits a measurement signal representative of the coating thickness to be determined. Said coating-thickness measurement means or the coating-thickness sensor may either be in contact with the measurement surface or positioned above the measurement surface without contact. The sensors may comprise components selected from a group of components comprising optical, inductive, capacitive components and the like.

In another preferred embodiment at least one processor means is provided which allows an allocation of the measurement signals at least of the first radiation detector means and/or the measurement signals of the distance measurement means and/or the coating-thickness measurement means to specified locations, in particular but not exclusively to the same location on the measurement surfaces.

In this way the corresponding signals or the data corresponding to those signals, respectively, can be captured to obtain matching information on the measurement surface to be examined or the area examined at a specified time. Preferably also data on the angular position of the device relative the measurement surface can be additionally determined.

The invention further relates to a method for determining the properties of surfaces wherein in a first step a radiation is transmitted onto a measurement surface through the second radiation means according to at least one of the preceding claims, in another step the radiation reflected off the measurement surface is received by means of a second radiation detector means of the type described above, and in another step the location on the radiation detector surface is determined on which a predetermined portion of the radiation impinges. Finally, a measurement number is output which is characteristic of the location on the radiaton detector surface on which the predetermined portion of the radiation impinges.

Preferably an indicator means displays the location on which a predetermined portion of the radiation impinges. For example the location can be displayed on which the maximum radiation intensity impinges or for example the area of the radiation detector surface on which light intensities in a predetermined range impinge, for example at 90 to 100% of the radiation.

Furthermore, for example the area of the radiation detector surface can be determined within which the radiation intensity lies above half of the maximum intensity, or for example above the x-th fraction of the maximum intensity.

Preferably the predetermined portion of the radiation/total radiation is the radiation impinging on the second radiation detector means. A predetermined portion is for example understood to mean, in the case of a circular or ellipsoid light beam, that portion of the beam surface within which the radiation intensity is higher than the x-th fraction of the maximum intensity. However, definitions differing therefrom, for example with reference to half the radiation intensity, are also possible.

Preferably the radiation is at maximum intensity at the location on which a predetermined portion of the radiation impinges.

It is further preferred to use at least one adjusting means of the type specified above for varying the angular position of the device relative the measurement surface such that the predetermined portion of the radiation impinges on a predetermined location of the radiation detector surface. This may for example but not exclusively be a geometrical center area of the radiation detector surface.

In another preferred method for determining the properties of surfaces, at least one distance measurement means according to at least one of the preceding claims is used to determine the distance from a predetermined geometrical location of the device to the measurement surface, and in reaction to the determined distance the angular position of the device relative the measurement surface is set at a target value. Preferably several distance measurement means are provided and by means of at least one adjusting means the angular position of the device relative the measurement surface is set such that the measurement surface has substantially predetermined, in particular equal distances from the individual geometrical locations of the device. In this way it can be guaranteed that the device is positioned substantially tangentially relative the measurement surface.

BRIEF DESCRIPTION OF THE DRAWINGS

Further advantages and embodiments of the device of the present invention can be taken from the figures. These show in:

FIG. 4 a schematic illustration of a radiation detector surface in another embodiment;

DETAILED DESCRIPTION

Figure 1:
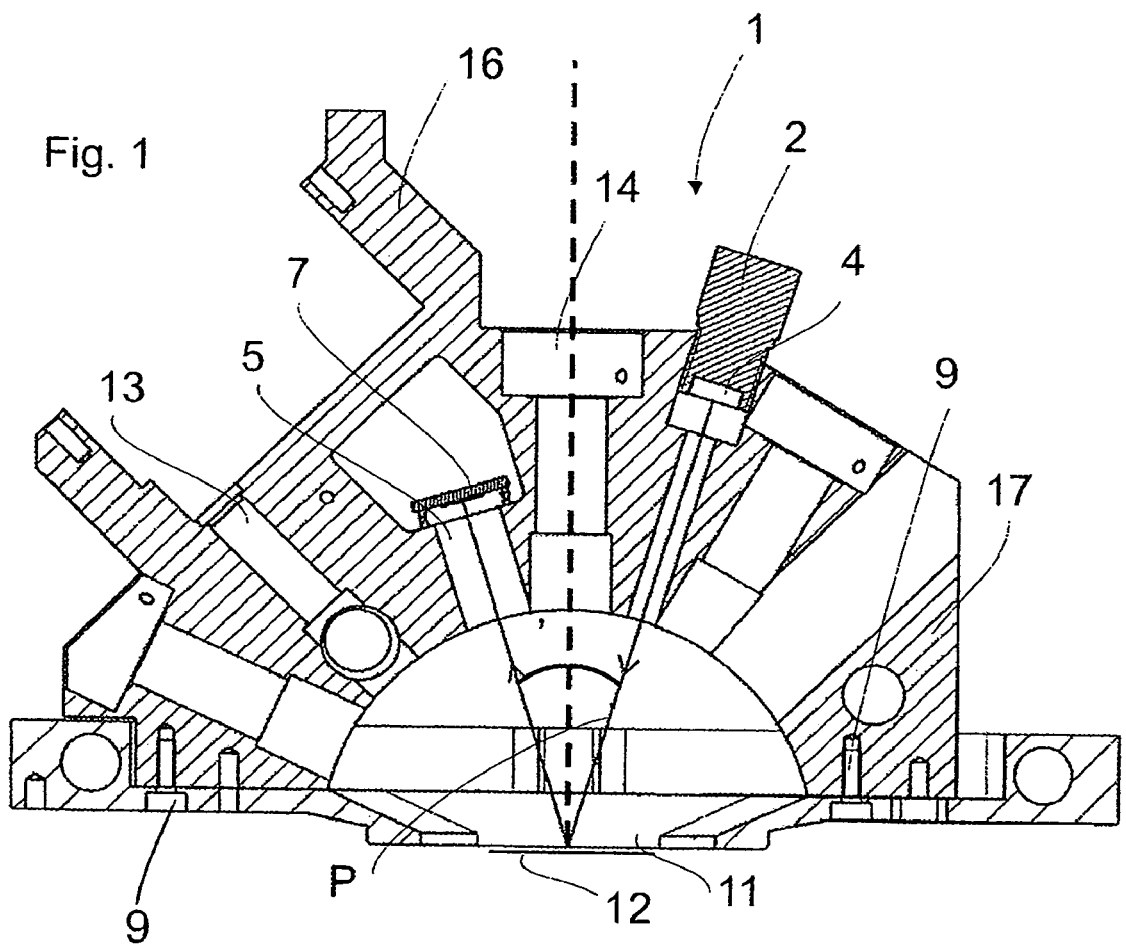
FIG. 1 a schematic illustration of the device of the present invention for determining the properties of surfaces in a first embodiment.

FIG. 1 shows the device 1 of the invention for determining the properties of surfaces. Reference numeral 13 relates to a first radiation means which emits radiation through an aperture 11 onto a measurement surface 12 lying beneath. A portion of the radiation reflected and/or diffused off the measurement surface 12 enters the first radiation detector means 14. Evaluating this radiation allows to draw conclusions about the properties of the measurement surface from the radiation and/or reflection ratio of the measurement surface.

As mentioned, attention must be paid to that the device be positioned at a predetermined angle, i.e. a predetermined position relative the measurement surface, in particular but not exclusively tangential relative the surface. In FIG. 1 this means that the dashed line is perpendicular to the measurement surface 12.

For this purpose a second radiation means 2 having a radiation source 4 is provided in this embodiment. Said radiation means 2 transmits at least partially directional radiation as indicated by arrow P at a predetermined angle α to the measurement surface. The at least partially directional radiation is reflected off the measurement surface at an angle α' and enters the second radiation detector means 5 which comprises at least one photosensitive component 7.

If the device is positioned tangentially relative the measurement surface 12, the angle α' at which the radiation is reflected off the measurement surface 11 relative the dashed line, is identical with the angle α.

If the device 1 is not positioned tangentially relative the measurement surface but at a different angle on the plane of the drawing, the angles α' and α are not identical.

If the angles α' and α are identical, a predetermined portion of the radiation emitting from the second radiation means impinges on a predetermined location of the detector surface 7. For example the portion of the radiation comprising the maximum intensity hits the geometrical center of the detector surface 7. This will be explained in more detail with reference to FIG. 2.

However, other variations in the angular position can also be detected such as a displacement out of the device relative the measurement surface 12 to the outside of the drawing.

In this case the beam reflected off the measurement surface would also not hit the geometrical center of the detector surface but would be displaced in a direction vertical to the plane of the drawing.

It is also conceivable to position the devices 4 and 5 along the dashed line but perpendicular above the measurement surface. In this case, beam splitters or the like may be provided, or the radiation source of the second radiation means can be positioned in the center of the radiation detector surface 7.

Figure 2:
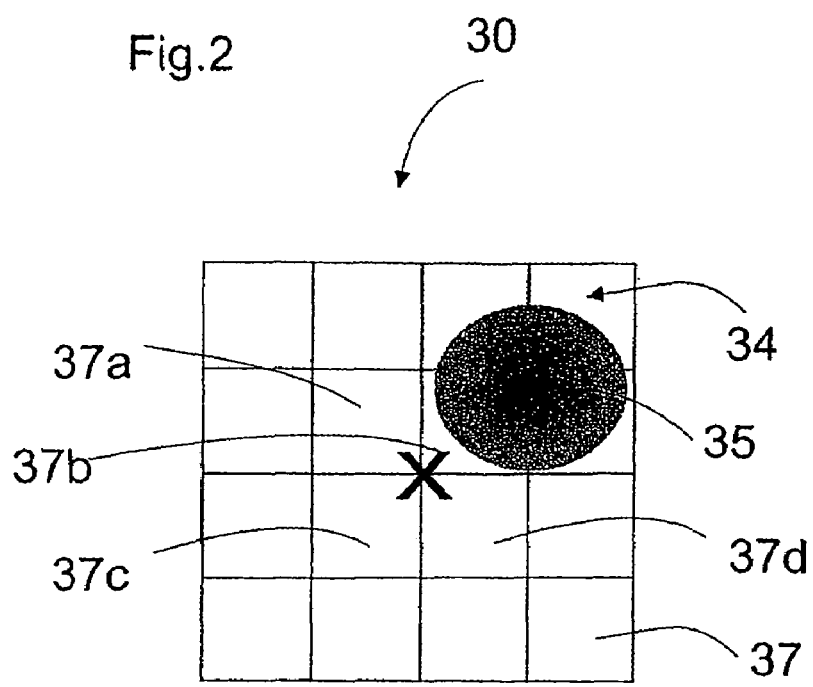
FIG. 2 a schematic illustration of the device of the present invention for determining the properties of surfaces in a second embodiment.

An adjusting means 9 can be used to vary the angular position of the device relative the measurement surface 12. This adjusting means may in particular but not exclusively be a micrometer screw or the like. Motorized control of the adjusting means is also within the scope of the invention. FIG. 2 is a schematic illustration of a radiation detector means 5 or a radiation detector surface 30, respectively. The beam reflected off the measurement surface 12 from the at least one second radiation means 2 or its radiation cross-section, respectively, is marked with the reference numeral 34. The areas of high radiation intensity are illustrated dark and the areas of lower radiation intensity bright.

The profile of the beam or ray bundle, respectively, emitting from the second radiation means may be substantially circular or ellipsoid in shape; this is, however, not mandatory. In practice, the actual profile may to a greater or lesser extent deviate from an ideal circle depending on the quality of the radiation source and the optics system.

In the example shown here, the beam or ray bundle, respectively, impinges substantially on the four photocells 37 shown at the top right in the Figure. Instead of the 16 photocells 37 shown here, more or fewer photocells may also be provided; the photocells may be arranged in a square array such as a 2×2, 3×3 . . . n×n array, or in a non-square array such as a 5×8, 1×4 etc. array.

The device in this example may be designed such that in case that the device is positioned tangentially relative the measurement surface the light bundle irradiates the four photocells 37a through 37d wherein the center of maximum light intensity is the point O.

For an indicator means, such impinging on the array could be displayed. By readjustment of the individual adjusting means, the device can be positioned or adjusted relative the measurement surface until the measurement patch 34 is in the center of the array.

Figure 3:
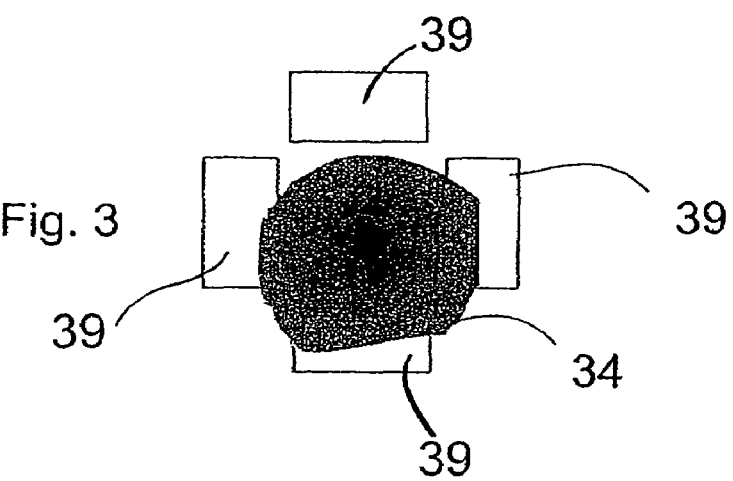
FIG. 3 a schematic illustration of a second radiation detector surface.

FIG. 3 is another embodiment of the radiation detector surface. In this case several capturing components or photocells 39 are arranged concentrically relative a predetermined point. This may for example be a point on which the radiation or its maximum intensity impinges when the device is positioned tangentially relative the measurement surface.

Instead of the four capturing components 39 shown here, more or fewer capturing components may be arranged. In this case the ray bundle 34 could be adjusted such that it impinges on the individual capturing components 39, the intensity is adjusted until it is substantially uniform. Unlike the bundle shown in FIG. 2, that shown in FIG. 3 is not concentric but different.

FIG. 4 shows another embodiment of the device of the invention for determining the properties of surfaces. Instead of the second radiation means and the second radiation detector means 5, this embodiment comprises at least one distance measurement means 15 which is illustrated only schematically in FIG. 2. These measurement means measure the distance of the devices or the distance of a not shown sensor to the measurement surface 12. Preferably several such distance measurement sensors are employed since the angular position of the device relative the measurement surface 12 can be determined from the measured distance values. This will be explained in more detail with reference to FIG. 5.

Figure 5:
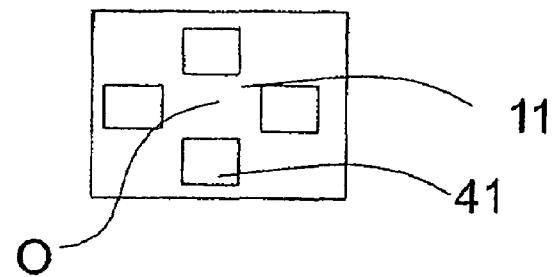
FIG. 5 a schematic illustration of an arrangement of a plurality of distance measurement means.

In FIG. 5 the reference numeral 11 relates to the measuring aperture beneath which the (not shown) measurement surface 12 is positioned.

Reference numeral 41 is a distance measurement means. If the measured distance of the individual distance measurement means from the measurement surface is substantially uniform, it can be assumed that the device is positioned tangentially relative the measurement surface. Several distance meters in the direction 41 may also be provided. Attention should be paid to that said distance measurement means be positioned as close as possible to a point 0 because the precision of the measurements will increase with the precision of the positioning of the individual measurement means.

The invention claimed is:

1. A device for determining the properties of surfaces having:
    at least one first radiation means having at least one first radiation source which directs a predetermined radiation towards a measurement surface;
    at least one first radiation detector means which captures at least a portion of the radiation reflected and/or diffused off the measurement surface and emits at least one measurement signal which is characteristic of the reflected and/or diffused radiation,
    wherein said device includes at least one measurement means which determines an angular position of the device relative to the measurement surface, said measurement means is composed of at least one second radiation means which directs at least partially directional radiation at a predetermined angle towards the measurement surface; and
    at least one second radiation detector means having a predetermined radiation detector surface which at least partially captures the radiation emitting from said second radiation means and reflected off the measurement surface and determines its position on the second radiation detector surface, wherein only selected areas of the second radiation detector surface are irradiated with radiation with radiation from the second radiation means, wherein the location of said irradiated areas depends on the angular position of the device relative to the measurement surface.

2. The device according to claim 1: wherein said device comprises at least one distance measurement means for determining the distance of a predetermined geometrical location of the device from the measurement surface.

3. The device according to claim 1, wherein it comprises at least one adjustment means by means of which the angular position of the device relative the measurement surface can be varied.

4. The device according to claim 1, wherein the predetermined radiation detector surface is irradiated not uniformly by radiation emitted from the second radiation means.

5. The device according to claim 1, wherein individual areas of said radiation detector surface are irradiated with radiation emitted from said second radiation means, and the location of said areas substantially depends on the angular position of the device relative the measuring surface.

6. The device according to claim 1, wherein
    said device comprises a plurality of adjusting means by means of which it is positioned relative the measurement surface in a preferred angular direction.

7. The device according to claim 1, wherein said second radiation detector means comprises a plurality of image-capturing components.

8. The device according to claim 1, wherein said plurality of image-capturing components of said second radiation detector means is distributed substantially concentrically around a predetermined geometrical center.

9. The device according to claim 1, wherein said second radiation detector means emits a signal which serves to adjust the angular position of said device relative the measurement surface.

10. The device according to claim 1, wherein said device comprises a measurement aperture through which the radiation impinging on the measurement surface passes.

11. The device according to claim 10, wherein a plurality of distance measurement means is provided which are positioned at predetermined positions relative the measurement aperture.

12. The device according to claim 2, wherein at least one distance measurement means comprises at least one component from a group of components including radiation sources, magnetic components, in particular but not exclusively magnet coils, and components utilizing the Hall effect.

13. The device according to claim 2, wherein each distance measurement means emits a signal characteristic of the distance from the predetermined geometrical location of the device to the measurement surface.

14. The device according to claim 1, wherein said second radiation means comprises at least one radiation source selected from a group of radiation sources comprising lasers, coherent and non-coherent semiconductor radiation sources, thermal radiation sources, in particular but not exclusively light bulbs, and halogen light bulbs.

15. The device according to claim 1, wherein the radiation emitted from said first radiation means is at least partially collimated by at least one radiation directing means.

16. The device according to claim 1, wherein at least one radiation directing means comprises at least one radiation directing component selected from a group of radiation directing components comprising lens elements, micro lens elements, micro lens arrays, diffracting components, reflector components, in particular but not exclusively parabolic reflectors, grating components, volume grating components, and holographic components.

17. The device according to claim 1, wherein at least said second radiation means comprises diaphragm means.

18. The device according to claim 1, wherein the radiation emitting from said second radiation means is repeatedly reflected in its optical path to the second radiation detector means.

19. The device according to claim 1, wherein the predetermined angle at which the radiation emitting from said second radiation means impinges on the measurement surface, is between 0 degrees and 90 degrees, preferred between 0 degrees and 60 degrees, particularly preferred between 0 degrees and 45 degrees and in particular between 0 degrees and 30 degrees.

20. The device according to claim 1, wherein at least said first radiation means comprises a radiation diffusor means selected from a group of radiation diffusor means comprising radiation diffusor disks, frosted glass disks, and diffusor films.

21. The device according to claim 1, wherein at least said first and said second radiation means are positioned in a housing above the measurement surface.

22. The device according to claim 1, wherein at least said first radiation source is variable in one radiation parameter which is selected from a group of parameters comprising radiation intensity, radiation wavelength, direction of radiation polarization, and temporal radiation intensity modulation.

23. The device according to claim 1, wherein said device is movable relative the measurement surface such that the distance between the radiation means and the measurement surface remains substantially constant.

24. The device according to claim 1, wherein at least one distance measurement means is provided which emits at least one measurement signal which is characteristic of the distance traveled of the relative movement between the device and the measurement surface.

25. The device according to claim 1, wherein at least one coating-thickness measurement means is provided for determining the coating thickness of the surface to be examined comprising at least one coating thickness sensor which emits a measurement signal representative of the coating thickness to be determined.

26. The device according to claim 25, wherein at least one processor means is provided which allows an allocation of the measurement signals of at least one of said radiation detector means, said distance measurement means, and said coating-thickness measurement means.

27. A method for determining the properties of surfaces including the following steps:
    emitting radiation onto a measurement surface through the second radiation means according to claim 1, wherein;
    capturing the radiation reflected off the measurement surface by means of the second radiation detector means according to claim 1;
    determining the location on the second radiation detector surface on which a predetermined portion of the radiation impinges;
    outputting at least one measurement number which is characteristic of the location on the second radiation detector surface on which the predetermined portion of the radiation impinges;
    displaying on an indicator means the measurement number which is characteristic of the location on the second radiation detector surface on which the predetermined portion of the radiation impinges; and
    varying the angular position of the device according to claim 1 relative to the measurement surface by at least one adjusting means, such that the predetermined portion of the radiation which is displayed as a measurement number on the indicator means impinges on a predetermined location on said second radiation detector surface.

28. The method according to claim 27, wherein the predetermined portion of the radiation is a major portion of the total of the radiation impinging on said second radiation detector means.

29. The method according to claim 27, wherein the radiation is of maximum intensity at the location on which a predetermined portion of the radiation impinges.

30. A method for determining the quality of surfaces wherein at least one distance measurement means according to at least one of the preceding claim 2 serves to determine the distance of a predetermined geometrical location between the device and the measurement surface, and in reaction to the determined distance the angular position of the device relative the measurement surface is adjusted to a predetermined value.

31. A device for determining the properties of surfaces having:
    at least one first radiation means having at least one first radiation source which directs a predetermined radiation towards a measurement surface;
    at least one first radiation detector means which captures at least a portion of the radiation reflected and/or diffused off the measurement surface and emits at least one measurement signal which is characteristic of the reflected and/or diffused radiation,
    wherein said device includes at least one measurement means which determines an angular position of the device relative to the measurement surface, said measurement means is composed of at least one second radiation means which directs at least partially directional radiation at a predetermined angle towards the measurement surface; and
    at least one second radiation detector means having a predetermined radiation detector surface which at least partially captures the radiation emitting from said second radiation means and reflected off the measurement surface and determines its position on the second radiation detector surface, wherein only selected areas of the second radiation detector surface are irradiated with radiation from the second radiation means, wherein the location of said irradiated areas depends on the angular position of the device relative to the measurement surface; and
    wherein at least one adjustment means is provided by means of which the angular position of the device relative to the measurement surface can be varied.

32. A device for determining the properties of surfaces having:
    at least one first radiation means having at least one first radiation source which directs a predetermined radiation towards a measurement surface;
    at least one first radiation detector means which captures at least a portion of the radiation reflected and/or diffused off the measurement surface and emits at least one measurement signal which is characteristic of the reflected and/or diffused radiation,
    wherein at least one adjustment means is provided by means of which the angular position of the device relative to the measurement surface can be varied;
    wherein said device includes at least one measurement means which determines an angular position of the device relative to the measurement surface, said measurement means is composed of at least one second radiation means which directs at least partially directional radiation at a predetermined angle towards the measurement surface;

at least one second radiation means is provided which directs at least partially directional radiation at a predetermined angle towards the measurement surface;

at least one second radiation detector means having a predetermined radiation detector surface which at least partially captures the radiation emitting from said second radiation means and reflected off the measurement surface and determines its position on the second radiation detector surface, wherein only selected areas of the second radiation detector surface are irradiated with radiation from the second radiation means, wherein the location of said irradiated areas depends on the angular position of the device relative to the measurement surface; and at least one indicator means connected to said second radiation detector means which outputs a measure for the location on said second radiation detector means on which a predetermined portion of radiation emitted from said second radiation detector means impinges, so as to enable a operator to set the adjustment means and thus adjust the device relative to the measurement surface such that it is tangential to the measurement surface in which position the radiation of the second radiation detector means impinging on the center of the second radiation detector surface and thus the indicator means display the radiation impinging on the center of the second radiation detector surface.

* * * * *